United States Patent
Hasegawa et al.

(10) Patent No.: US 9,930,294 B2
(45) Date of Patent: Mar. 27, 2018

(54) HANDPIECE WITH BUILT-IN CAMERA AND DENTAL TREATMENT METHOD USING HANDPIECE

(71) Applicant: THE YOSHIDA DENTAL MFG. CO., LTD., Tokyo (JP)

(72) Inventors: Takeshi Hasegawa, Tokyo (JP); Michizo Yamanaka, Tokyo (JP)

(73) Assignee: The Yoshida Dental Mfg. Co., Ltd., Tokyo (JP)

( * ) Notice: Subject to any disclaimer, the term of this patent is extended or adjusted under 35 U.S.C. 154(b) by 302 days.

(21) Appl. No.: 14/424,525

(22) PCT Filed: Aug. 30, 2013

(86) PCT No.: PCT/JP2013/073261
§ 371 (c)(1),
(2) Date: Feb. 27, 2015

(87) PCT Pub. No.: WO2014/034830
PCT Pub. Date: Mar. 6, 2014

(65) Prior Publication Data
US 2015/0222856 A1    Aug. 6, 2015

(30) Foreign Application Priority Data
Aug. 31, 2012  (JP) .................. 2012-192140

(51) Int. Cl.
*H04N 7/18* (2006.01)
*A61C 1/08* (2006.01)
(Continued)

(52) U.S. Cl.
CPC ................. *H04N 7/18* (2013.01); *A61B 1/00* (2013.01); *A61B 1/00165* (2013.01);
(Continued)

(58) Field of Classification Search
CPC .......... H04N 7/18; H04N 5/2252; H04N 5/44; G02B 13/0015; G06T 7/0012;
(Continued)

(56) References Cited

U.S. PATENT DOCUMENTS 4,182,038 A * 1/1980 Fleer ...................... A61C 1/08
433/126
4,772,093 A * 9/1988 Abele ................ A61B 1/00096
385/117

(Continued)

FOREIGN PATENT DOCUMENTS

JP          5-31126       2/1993
JP          5-111497      5/1993
(Continued)

*Primary Examiner* — Jay Patel
*Assistant Examiner* — Joseph Suh
(74) *Attorney, Agent, or Firm* — Norris McLaughlin & Marcus, P.A.

(57) ABSTRACT

A handpiece with a built-camera includes a micromotor-driven handpiece body which includes a cutting tool attached to a head portion thereof, a light receiving port at a position near the cutting tool, a grip portion detachably connected to the handpiece body and a color camera module which is stored inside the handpiece body. The handpiece with the built-in camera further includes an objective lens which faces the light receiving port and a rod fiber which is attached to an inner wall portion of the handpiece body with an incidence end of the rod fiber facing the objective lens and an exit end of the rod fiber facing a condensing lens unit.

15 Claims, 18 Drawing Sheets

(51) Int. Cl.
*A61B 1/00* (2006.01)
*A61B 1/04* (2006.01)
*A61B 1/06* (2006.01)
*A61B 1/247* (2006.01)
*A61B 1/24* (2006.01)
*G02B 13/00* (2006.01)
*G06T 7/00* (2017.01)
*H04N 5/225* (2006.01)
*H04N 5/44* (2011.01)

(52) U.S. Cl.
CPC ............ *A61B 1/042* (2013.01); *A61B 1/0607* (2013.01); *A61B 1/0676* (2013.01); *A61B 1/0684* (2013.01); *A61B 1/24* (2013.01); *A61B 1/247* (2013.01); *A61C 1/08* (2013.01); *G02B 13/0015* (2013.01); *G06T 7/0012* (2013.01); *H04N 5/2252* (2013.01); *H04N 5/44* (2013.01); *G06T 2207/30036* (2013.01)

(58) Field of Classification Search
CPC ... G06T 2207/30036; A61B 1/24; A61B 1/00; A61B 1/0607; A61B 1/0676; A61B 1/247; A61B 1/0684; A61B 1/00165; A61B 1/042; A61C 1/08
See application file for complete search history.

(56) References Cited

U.S. PATENT DOCUMENTS

| | | | | |
|---|---|---|---|---|
| 5,049,070 A * | 9/1991 | Ademovic | ............ | A61B 1/042 348/66 |
| 6,102,695 A | 8/2000 | Rosenstatter | | |
| 6,104,553 A * | 8/2000 | Nagahara | ............ | G02B 9/04 359/691 |
| 2003/0012461 A1 | 1/2003 | Satoh et al. | | |
| 2005/0003323 A1* | 1/2005 | Katsuda | ............ | A61B 1/00089 433/29 |
| 2006/0116669 A1* | 6/2006 | Dolleris | ............ | A61B 18/203 606/17 |
| 2008/0082000 A1* | 4/2008 | Thoms | ............ | A61B 1/00177 600/476 |
| 2008/0160477 A1* | 7/2008 | Stookey | ............ | A61B 1/00041 433/31 |
| 2010/0167235 A1* | 7/2010 | Vercellotti | ............ | A61B 17/1615 433/86 |
| 2011/0270241 A1 | 11/2011 | Boutoussov | | |
| 2012/0040305 A1* | 2/2012 | Karazivan | ............ | A61B 1/00087 433/29 |
| 2012/0200849 A1* | 8/2012 | Balducci | ............ | G01N 21/8806 356/240.1 |
| 2012/0315598 A1* | 12/2012 | Kim | ............ | A61C 1/05 433/132 |
| 2013/0034825 A1* | 2/2013 | Phillips | ............ | A61B 1/00016 433/29 |
| 2013/0283840 A1* | 10/2013 | Kakizaki | ............ | B60H 1/00064 62/276 |

FOREIGN PATENT DOCUMENTS

| | | |
|---|---|---|
| JP | 6-510678 | 12/1994 |
| JP | 7-328032 | 12/1995 |
| JP | 9-56730 | 3/1997 |
| JP | 9-140664 | 6/1997 |
| JP | 10-66677 | 3/1998 |
| JP | 2003-029159 | 1/2003 |
| JP | 2004-039285 | 2/2004 |
| JP | 2006-81842 | 3/2006 |
| JP | 2009-512463 | 3/2009 |
| JP | 2010-104652 | 5/2010 |
| JP | 2012-10849 | 1/2012 |

* cited by examiner

HANDPIECE WITH BUILT-IN CAMERA AND DENTAL TREATMENT METHOD USING HANDPIECE

BACKGROUND OF THE INVENTION

The present invention relates to a handpiece with a built-in camera and a dental treatment method using the handpiece.

In the field of dental treatment, when a carious tooth or the like in the mouth is treated, in many cases, an operator uses a cutting handpiece for cutting and removing decayed portions of the tooth structure while visually observing the treatment site. In this case, the operator generally observes the distal wall of a tooth or the like, which is difficult to be visually observed, using a dental mirror.

In addition, during a procedure of the treatment site such as the cutting, a dental treatment device in which an illumination mechanism which illuminates the inside of the mouth is provided in a handheld member of this type of dental treatment instrument is used. The applicant developed and suggested Patent Documents 5 and 6 as the illumination mechanism used in this type of dental treatment device.

In recent years, a handpiece having an image photographing function for observing the inside of the mouth is also developed.

For example, in JP 2009-512463 W, a device is disclosed in which a medical procedure handpiece (laser handpiece) which outputs electromagnetic energy and an image capturing auxiliary device which is attached to and detached from the laser handpiece to be used are combined.

However, in the case of JP 2009-512463 W, the laser handpiece itself does not include image capturing means therein but the image capturing auxiliary device has to be attached whenever the image of a treatment side is to be captured during the use of the laser handpiece, which results in complexity during the use by an operator.

In JP 2006-81842 A, an auxiliary for fluorescence photography is disclosed which is combined with an existing handpiece for dental photography.

However, in the case of JP 2006-81842 A, since the auxiliary for fluorescence photography is combined with the handpiece for dental photography, the combination is clearly different from a configuration in which an image photographing function is added to a handpiece for cutting a treatment site.

In JP 09-140664 A, a dental camera for observing the inside of a mouth is suggested which is configured such that a head portion is provided at the tip end of a handpiece 1, an objective lens and a CCD for converting the image taken by the objective lens into an electrical signal are disposed at the head portion, the electrical signal converted by the CCD is transferred to an image display apparatus, an affected area in a mouth is illuminated by light emitted from the light-emitting end of a light guide.

However, even the case of JP 09-140664 A is not applied to the configuration in which an image photographing function is added to a handpiece for cutting a treatment site.

In JP 07-328032 A, a dental work handpiece provided with an image recording device including an image conductor and an optical waveguide is suggested. The dental work handpiece provided with the image recording device has a configuration in which the image conductor (3) and the optical waveguide (4) are assembled into the handpiece (1).

In the case of the dental work handpiece of JP 07-328032 A, it is estimated that the image of an affected area in the mouth can be recorded. However, this is merely a general configuration in which the optical waveguide (4) for illuminating the affected area is provided as a separate system from the image conductor (3) in the body.

SUMMARY OF THE INVENTION

A problem to be solved by the invention is that a handpiece with a built-in camera, in which a color camera function is provided in a handpiece for cutting a treatment site so as to allow a treatment to be performed while viewing a clear color image of a treatment site which is difficult to be seen normally, such as the distal wall of a tooth, is not present.

The invention is mainly characterized in that a handpiece with a built-in camera includes: a handpiece body which includes a cutting tool attached to a head portion thereof, and a light receiving port provided at a position near the cutting tool; a grip portion which is detachably connected to the handpiece body; and a color camera module which is stored inside the handpiece body, wherein the color camera module includes a camera unit having a condensing lens unit and a color image sensor that outputs a color image signal, and an arbitrary number of light-emitting elements which are circularly arranged around a periphery of the camera unit, an objective lens which faces the light receiving port provided in the head portion, and an optical transmission body which is disposed in the handpiece body in a state in which an incidence end thereof faces the objective lens and an exit end thereof faces the condensing lens unit are included, and a photographing optical system which transmits imaging light of an affected area to the camera unit via the objective lens and the optical transmission body is included.

According to a first aspect of the invention, it is possible to provide a handpiece with a built-in camera which allows a treatment to be performed while viewing a clear color image of a treatment site, which is difficult to be seen normally, such as a distal wall of a tooth, on the basis of the configuration including the camera unit having the condensing lens unit and the color image sensor, the objective lens that faces the light receiving port provided in the head portion, and the optical transmission body disposed in a state in which the incidence end faces the objective lens and the exit end faces the condensing lens unit, in the handpiece body.

According to a second aspect of the invention, it is possible to provide a handpiece with a built-in camera which allows a treatment to be performed while viewing a clear color image of a treatment site, which is difficult to be seen normally, such as a distal wall of a tooth, on the basis of the configuration including the camera unit having the condensing lens unit and the color image sensor, the objective lens that faces the light receiving port provided in the head portion, and the rod fiber disposed in a state in which an incidence end thereof faces the objective lens and an exit end thereof faces the condensing lens unit, in the handpiece body.

According to a third aspect of the invention, it is possible to provide a handpiece with a built-in camera which allows a treatment to be performed while viewing a clear color image of a treatment site, which is difficult to be seen normally, such as a distal wall of a tooth, on the basis of the configuration including the camera unit having the condensing lens unit and the color image sensor, the objective lens that faces the light receiving port provided in the head portion, and the rod fiber disposed in a state in which an incidence end thereof faces the objective lens and an exit end thereof faces the condensing lens unit, in the handpiece body.

According to a fourth aspect of the invention, in the handpiece with a built-in camera of any one of the first to third aspects of the invention, since the focus range of the condensing lens unit is set to 3 to 50 mm, a range in which a clear color image of an affected area can be obtained is wide, and a handpiece with a built-in camera having a high practical value can be provided.

According to a fifth aspect of the invention, in the handpiece with a built-in camera of any one of the second to fourth aspects of the invention, since an interval between the objective lens and the incidence end of the rod fiber is configured to allow the photographing light from the objective lens to be substantially received by a light receiving angle of the rod fiber, and an interval between the exit end of the rod fiber and the condensing lens unit is configured to allow light that exits from the rod fiber to be substantially received by the viewing angle of the condensing lens unit, photographing light which is incident onto the objective lens can be reliably guided to the color image sensor and conversion of the light into a color image can be realized. Therefore, it is possible to provide a handpiece with a built-in camera having a high practical value.

According to a sixth aspect of the invention, in the handpiece with a built-in camera of any one of the first to fifth aspects of the invention, since fog in a region of the light receiving port can be removed, and thus it is possible to provide a handpiece with a built-in camera capable of imaging a clear color image.

According to a seventh aspect of the invention, in the handpiece with a built-in camera of any one of the first to fifth aspects of the invention, by an air curtain effect of the air ejected from an opening of an anti-fogging air flow passage, fogging of the light receiving port caused by spray or water drops generated during the cutting work by the handpiece with a built-in camera is prevented. Therefore, it is possible to provide a handpiece with a built-in camera capable of securing visibility.

According to an eighth aspect of the invention, in the handpiece with a built-in camera of any one of the first to seventh aspects of the invention, the number of internal electric cables is reduced, and thus the number of occurrences of an inconvenient circumstance such as cable disconnection can be reduced.

According to a ninth aspect of the invention, regarding a dental treatment of a treatment site, a treatment in which the operational effects of the handpiece with a built-in camera of the first to eighth aspects of the invention are exhibited and can be realized.

DETAILED DESCRIPTION OF THE INVENTION

An object of the invention is to provide a handpiece with a built-in camera which allows a treatment to be performed while viewing a clear color image of a treatment site, which is difficult to be seen normally, such as a distal wall of a tooth, and this object is realized by a configuration in which a handpiece with a built-in camera includes: a handpiece body which includes a cutting tool attached to a head portion thereof, and a light receiving port provided at a position near the cutting tool; a grip portion which is detachably connected to the handpiece body; and a color camera module which is stored inside the handpiece body, wherein the color camera module includes a camera unit having a condensing lens unit and a color image sensor that outputs a color image signal, and an arbitrary number of light-emitting elements which are circularly arranged around a periphery of the camera unit, an objective lens which faces the light receiving port provided in one head portion, and a rod fiber which is disposed in the handpiece body in a state in which an incidence end thereof faces the objective lens and an exit end thereof faces the condensing lens unit are included, and a photographing optical system which transmits imaging light of an affected area to the camera unit via the objective lens and the rod fiber is included.

Hereinafter, a handpiece with a built-in camera according to an embodiment of the invention will be described in detail with reference to the drawings.

Embodiment 1

Figure 1:
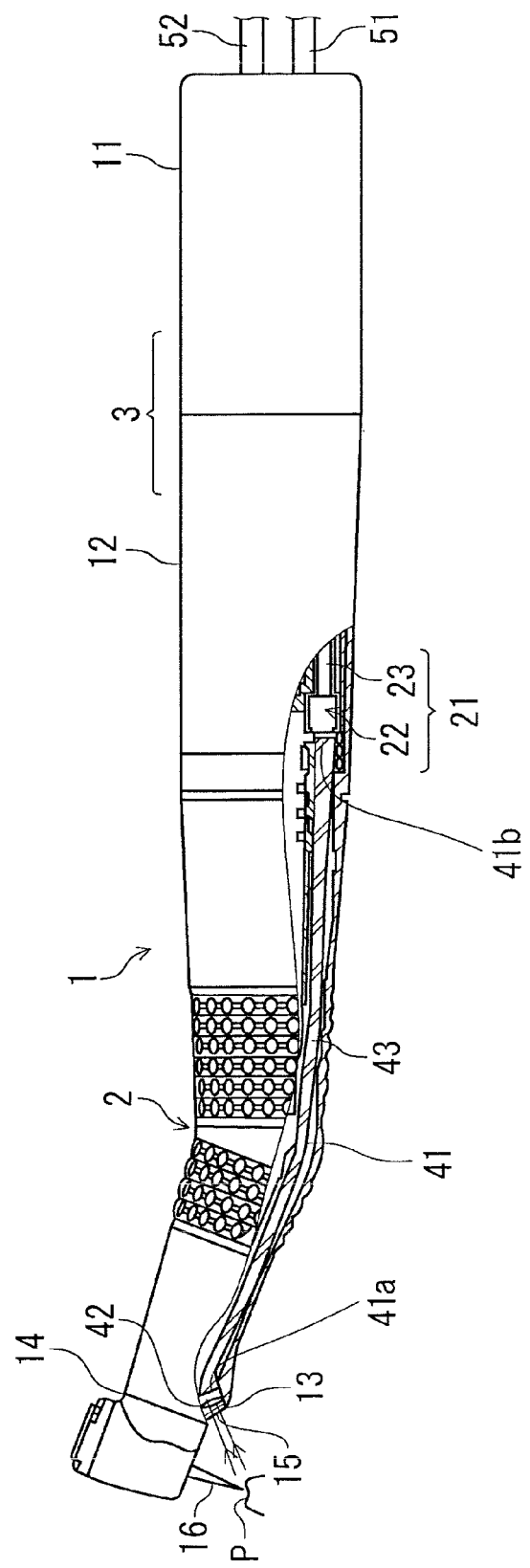
FIG. 1 is a partial cut-away front view of a handpiece with a built-in camera according to Embodiment 1 of the invention.
Figure 2:
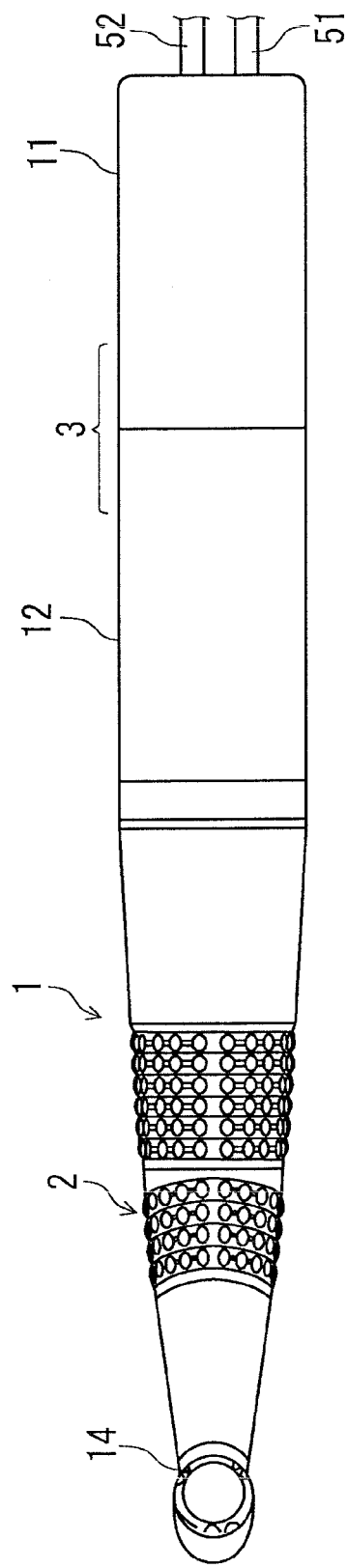
FIG. 2 is a plan view of the handpiece with a built-in camera according to Embodiment 1.

A handpiece 1 with a built-in camera of Embodiment 1 is configured of a micromotor type, and as illustrated in FIGS. 1 and 2, includes a grip portion 3 which is substantially cylindrical, and a handpiece body 2 which is detachable fitted and joined to the other end side of the grip portion 3 by bearings so as to be disposed coaxially therewith and to be rotatable.

The handpiece body 2 includes a handpiece body tube portion 12 which has a substantially cylindrical shape to which a head portion 14 having a connection tool 16 attached to the tip end thereof and a light receiving port 13 is fixed and is bent at an intermediate position with a predetermined angle.

In addition, the grip portion 3 includes a substantially cylindrical connection tube portion 11 which is detachably joined to the handpiece body tube portion 12 by bearings so as to be disposed coaxially therewith and to be rotatable, and a hose connection portion with a signal output cable 51 and a light-emitting element driving cable 52 provided therein on the other end side of the connection tube portion 11.

As illustrated in FIG. 1, the inner peripheral portion of the lower portion of the handpiece 1 with a built-in camera of Embodiment 1 on the inside of the handpiece body 2 stores a color camera module 21 for imaging an image of, for example, an affected area in a mouth, and includes an imaging optical system 41 having a light incidence end 41a that faces the light receiving port 13 provided in the head portion 14 and a light exit end 41b that faces the color camera module 21.

Figure 3:
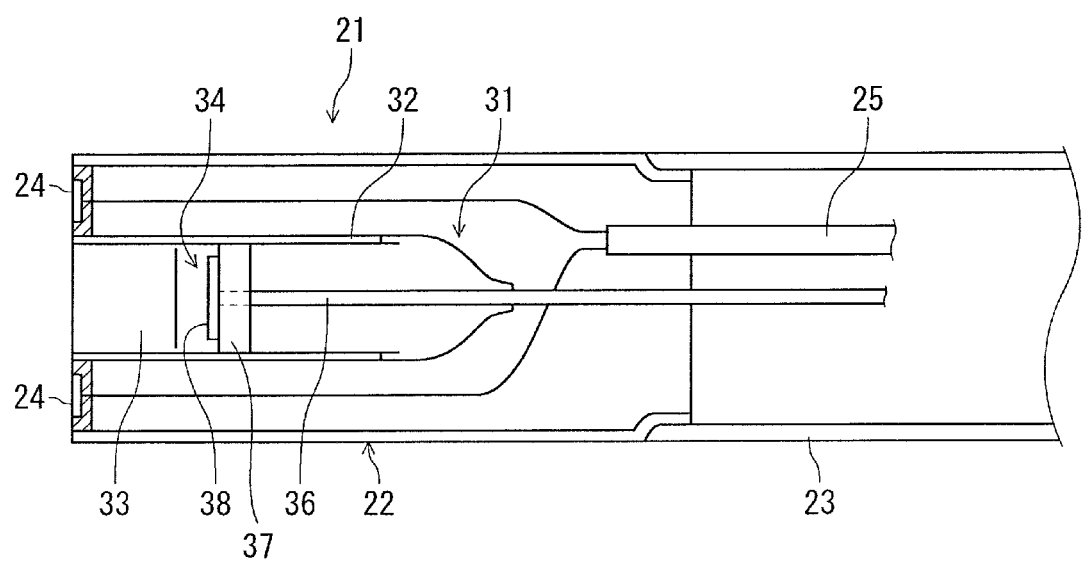
FIG. 3 is a schematic cross-sectional view illustrating a camera module of the handpiece with a built-in camera according to Embodiment 1.
Figure 4:
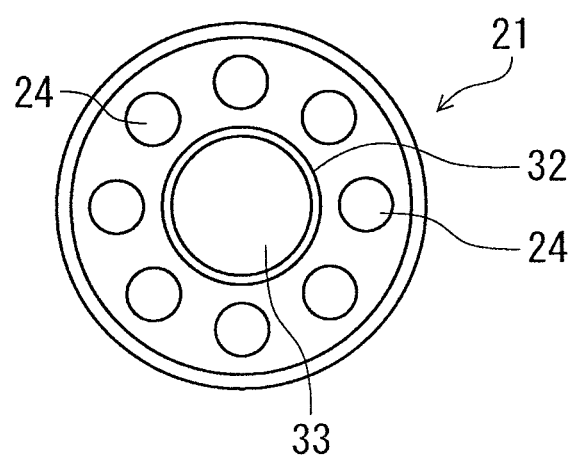
FIG. 4 is a schematic side view of the camera module of the handpiece with a built-in camera according to Embodiment 1.

As illustrated in FIGS. 3 and 4, the color camera module 21 has a configuration in which a cylindrical camera bead portion 22 is provided, a camera unit 31 is disposed over the inside from the tip end surface thereof, and an arbitrary number of (for example, eight) light-emitting elements (Light Emitting Diodes (LEDs)) 24 (for example, a driving voltage of DC 3.3 V) are circularly arranged around the end surface of the camera unit 31. A camera cable 23 is connected to the camera head portion 22.

As the arrangement of the light-emitting elements 24, in addition to the above-described case, a configuration in which light-emitting elements that can emit illumination light to be incident onto a rod fiber 43 are arranged on the outside of the end surface of the camera unit 31 may be employed, and the number of light-emitting elements being arranged may be arbitrarily set to 1, 2, 4, . . . , 12, . . . , or the like. Furthermore, the arrangement form is not particularly limited.

Figure 5:
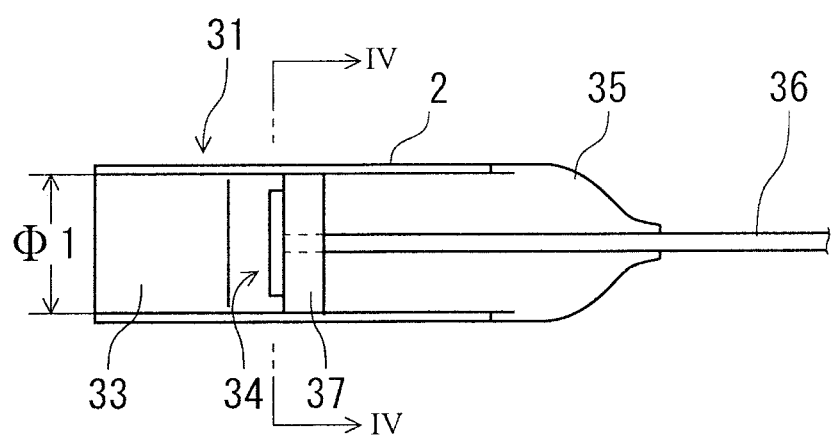
FIG. 5 is a schematic cross-sectional view illustrating a camera unit of the handpiece with a built-in camera according to Embodiment 1.
Figure 6:
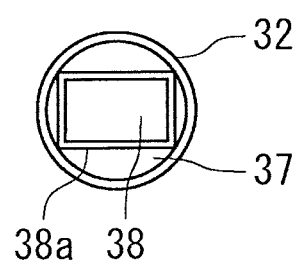
FIG. 6 is a cross-sectional view taken along line VI-VI of FIG. 5.

The camera unit 31 will be described in detail with reference to FIGS. 5 and 6.

The camera unit 31 includes a cylindrical support tube 32 having, for example, a diameter of 1.2 mm, an inside diameter of about 1.1 mm, and a length of 3 mm, a condensing lens unit 33 which has a light incidence end that is disposed to face one end surface of the support tube 32 and has a diameter of $\Phi1=1.1$ mm, an imaging unit 34 which is disposed to oppose the condensing lens unit 33 with a predetermined interval therebetween in the support tube 32, a cover member 35 which is fitted in a range from the other end surface side of the support tube 32 to the inside of the support tube 32, and a signal cable 36 which is connected to the imaging unit 34 and is drawn toward the rear side through the cover member 35.

The imaging unit 34 includes a disk-like support substrate 37 having a diameter of 1.1 mm, which is fixed in a state in which the center thereof is coincident with the optical axis of the condensing lens unit 33 in the support tube 32, and a color image sensor (Complementary Metal Oxide Semiconductor (CMOS)) 38 in which color pixels are arranged with a pixel count of 320×240 pixels on the surface of a sensor substrate 38a having external dimensions of 0.84×0.74 mm and a thickness of 0.1 mm and the center portion thereof is in a state of being coincident with the optical axis of the condensing lens unit 33. One end side of the signal cable 36 is connected to the color image sensor 38, and the other end side thereof is drawn toward the rear side through the support substrate 37 and the cover member 35.

As the condensing lens unit 33, a condensing lens unit having optical characteristics of, for example, a viewing angle of 70 degrees and a focus range of 3 to 50 mm is employed.

One end of a light-emitting element cable 25 is connected to the light-emitting elements 24 arranged around the end surface of the camera unit 31, and the light-emitting element cable 25 is stored in the camera cable 23 together with the signal cable 36 and is drawn toward the grip portion 3 side.

As illustrated in FIG. 1, in the imaging optical system 41, the light incidence end faces the light receiving port 13 provided in the head portion 14, and the light exit end faces the color camera module 21.

That is, the imaging optical system 41 includes an objective lens 42 which is disposed inside a transparent glass plate 15 attached to the light receiving port 13, and the rod fiber 43 which is an optical transmission body disposed in a state of allowing the light incidence end thereof to face the objective lens 42, extending in the handpiece body 2 along the inner peripheral portion of the lower portion thereof, and allowing the light exit end thereof to face the condensing lens unit 33.

Figure 7:
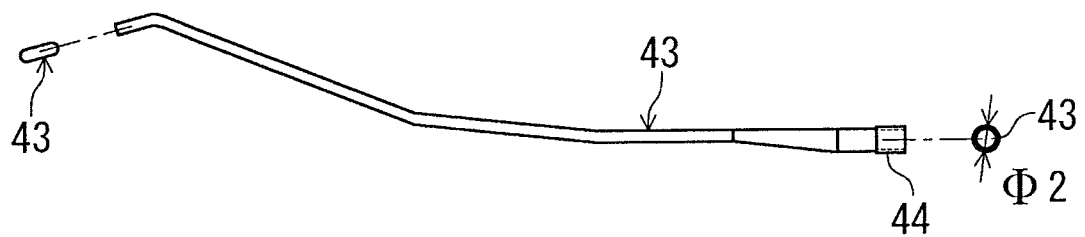
FIG. 7 is an enlarged explanatory view of a rod fiber in Embodiment 1.

An example of the specific configuration of the rod fiber 43 is illustrated in FIG. 7.

As the rod fiber 43, a rod fiber having a step-index type structure in which multi-component glass is used for all of the core, the cladding, and the skin tube to provide different refractive indexes in stages, and having optical characteristics of a light receiving angle of about 70 degrees and a numerical aperture (NA) of 0.57 is employed.

In addition, in the rod fiber 43, the shape of the light exit end thereof has, for example, a fiber diameter of $\Phi2$=about 2.4 mm, the outer periphery of the end portion thereof is covered with a stainless steel cylindrical body 44, and the shape of the light incidence end is, for example, art oval shape having a major axis of about 3.6 mm and a minor axis of about 1.35 mm.

Moreover, the rod fiber 43 has a specification with autoclave resistance of within 90% with respect to an initial transmittance after 350 cycles under the autoclave conditions of 135° C., 100% RH, and 3 minutes.

Figure 8:
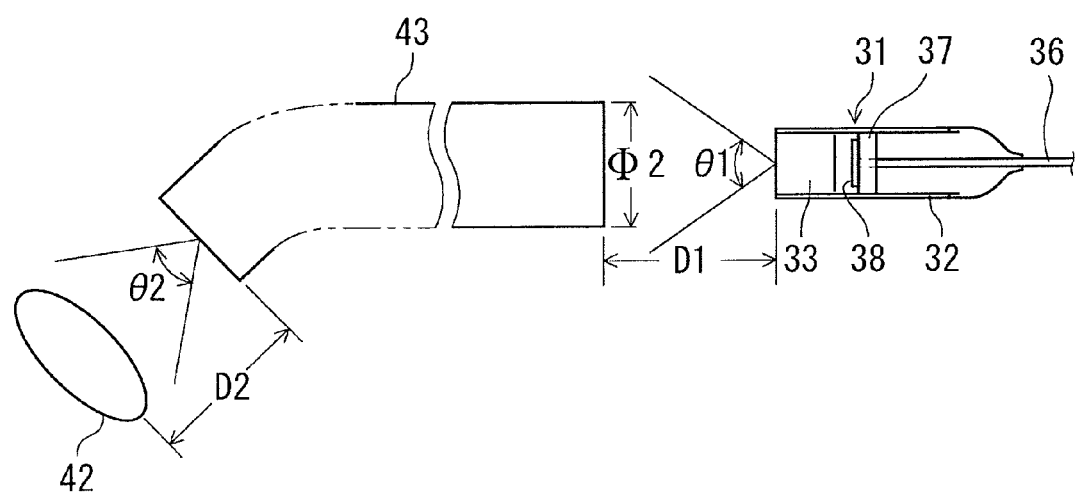
FIG. 8 is an explanatory view of an optical arrangement of the camera unit, the rod fiber, and an objective lens in Embodiment 1.

Here, the camera unit 31 included in the color camera module 21, the rod fiber 43, and the objective lens 42 will be described in detail with reference to the enlarged explanatory view of FIG. 8.

Regarding the relationship between the light exit end of the rod fiber 43 and the condensing lens unit 33 of the camera unit 31, a configuration in which a condensing lens unit having a viewing angle of $\theta1=70$ degrees is used as the condensing lexis unit 33, and an interval D1 between the light incidence surface of the condensing lexis unit 33 and the light exit end of the rod fiber 43 is set to about 3 mm by causing the diameter of the light exit end of the rod fiber 43 to be Φ2=about 2.4 mm is employed. Therefore, a beam that exits from the light exit end of the rod fiber 43 can be received by the range of the viewing angle of the condensing lens unit 33 and thus can be guided to the condensing lens unit 33 without hindrance.

On the other hand, regarding the relationship between the objective lens 42 and the light incidence end of the rod fiber 43, since the light receiving angle η2 of the rod fiber 43 is about 70 degrees, for example, a convex lens having a lens diameter of 3 mm and a focal length of 3 mm is used as the objective lens 42 and the interval between the objective lens 42 and the light incidence end of the rod fiber 43 is set to about D2=3 mm. Therefore, imaging light that is incident onto the light incidence end of the rod fiber 43 via the objective lens 42 can be received by the range of the light receiving angle, and thus can be guided to the light incidence end of the rod fiber 43 without hindrance.

With this configuration, according to Embodiment 1, photographing light which is incident onto the objective lens 42 from an affected area P can be reliably guided to the color image sensor 38 and conversion of the light into a color image can be realized. Therefore, it is possible to provide the handpiece 1 with a built-in camera having a high practical value.

In addition, according to Embodiment 1, since the focus range of the condensing lens unit 33 is set to 3 to 50 mm, when a treatment is performed by using the handpiece 1 with a built-in camera, a range in which a clear color image of the affected area P can be obtained is wide. Even from this point, a handpiece with a built-in camera having a high practical value can be provided.

Next, the processing structure of the light-emitting element cable 25 and the signal cable 36 stored in the camera cable 23 will be described.

For the light-emitting element cable 25 and the signal cable 36, a configuration may be employed in which a contact portion for the light-emitting element cable 25 and a contact portion for the signal cable 36 are respectively provided between the opposing end surfaces of the joining portions of the connection tube portion 11 and the grip portion 3 although not illustrated so that an image signal from the color image sensor 38 is sent from the signal cable 36 via the contact portion and is extracted to the outside of the handpiece 1 with a built-in camera by the signal output cable 51 introduced into the grip portion 3 so as to be transmitted to a drive control unit 61, and light-emitting element driving current supplied from the drive control unit 61 is supplied to the light-emitting element cable 25 from the light-emitting element driving cable 52 introduced into the grip portion 3 via the contact portion.

Figure 9:
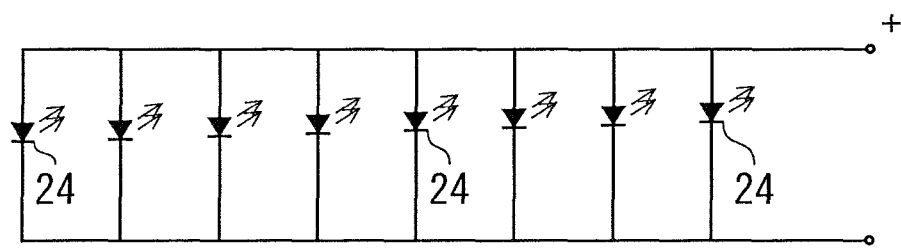
FIG. 9 is a circuit diagram illustrating a driving circuit of light-emitting elements in Embodiment 1.

FIG. 9 illustrates a driving circuit of the light-emitting elements 24, which is configured so that, for example, eight light-emitting elements 24 are connected in series and a DC voltage supplied from a light-emitting element power source 63 via the light-emitting element cable 24 is applied between the anode and the cathode of each of the light-emitting elements 22 to turn on and off the light-emitting elements 22.

Figure 10:
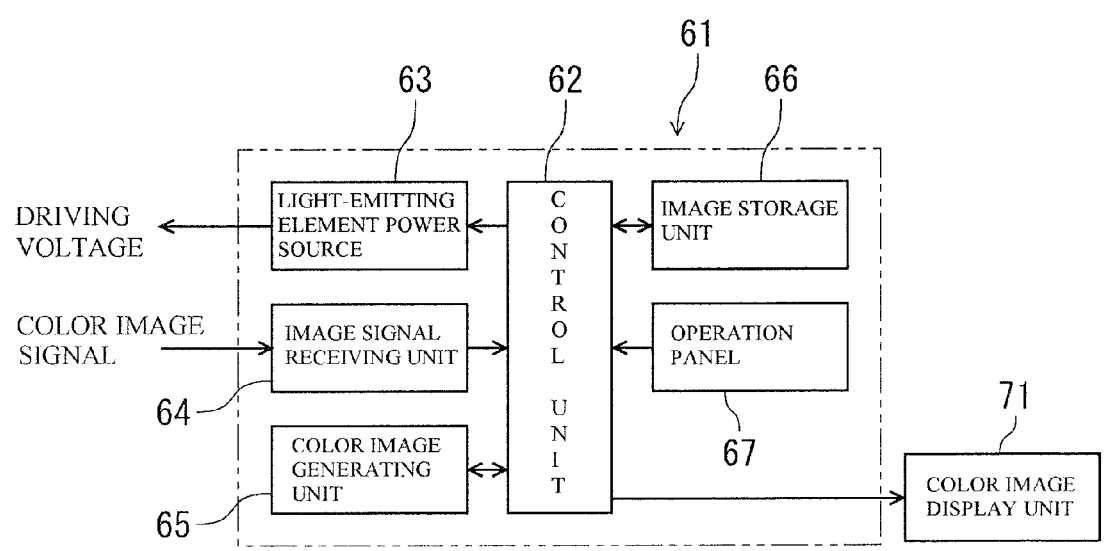
FIG. 10 is a block diagram illustrating the schematic configuration of a drive control unit in Embodiment 1.

Next, the schematic configuration of the drive control unit 61 will be described with reference to FIG. 10.

The drive control unit 51 includes a control unit 62 which controls the overall operations of the handpiece 1 with a built-in camera, the light-emitting element power source 63 which supplies a driving voltage (for example, DC 3.3 V) to each of the light-emitting elements 24, an image signal receiving unit 64 which receives an image signal from the camera unit 31, a color image generating unit 65 which generates a color image of the arrangement of teeth in a mouth on the basis of the received image signal, an image storage unit 66 which stores the generated color image, and an operation panel 67 having various operation buttons and the like necessary for the operation of the handpiece 1 with a built-in camera.

The handpiece 1 with a built-in camera of Embodiment 1 further includes a color image display unit 71 configured as a color liquid crystal display or the like, which displays the color image imaged by the camera unit 31 and generated by the color image generating unit 65 on the screen.

Figure 11:
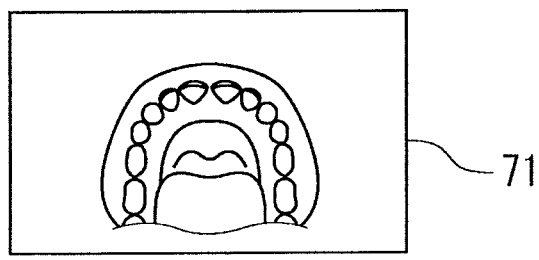
FIG. 11 is a diagram illustrating a display example of a color image by a color image display unit in Embodiment 1.

Accordingly, as illustrated in FIG. 11, a part of the distal wall of the arrangement of teeth in a mouth, which is difficult to be seen by the naked eyes of an operator, can also be checked by the color image.

In Embodiment 1, description of a driving system of the cutting tool 16 will be omitted, Embodiment 2

Figure 12:
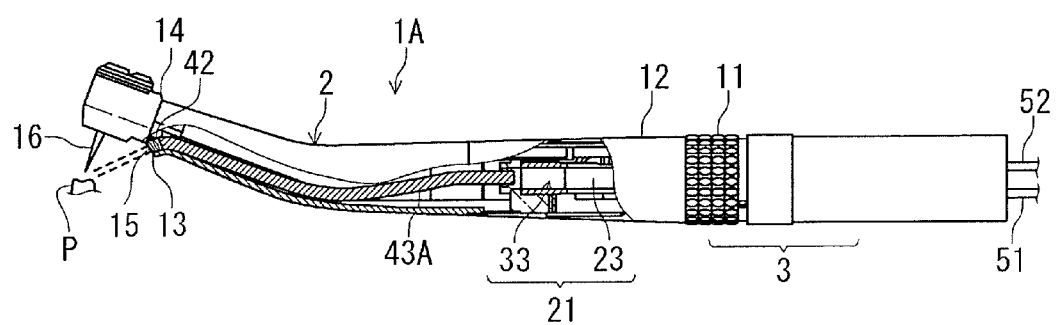
FIG. 12 is a partial cut-away front view of a handpiece with a built-in camera according to Embodiment 2 of the invention.
Figure 13:
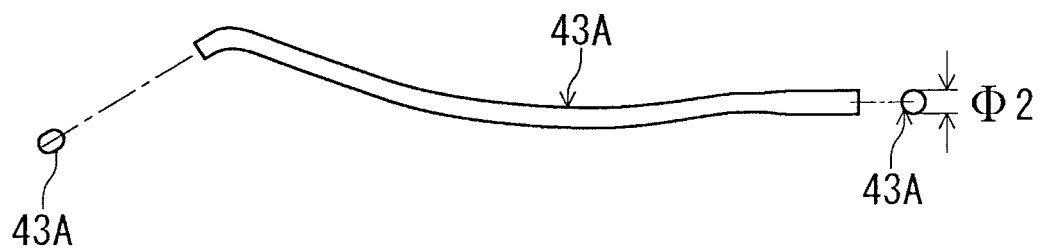
FIG. 13 is an enlarged explanatory view of a rod fiber in Embodiment 2.
Figure 18:
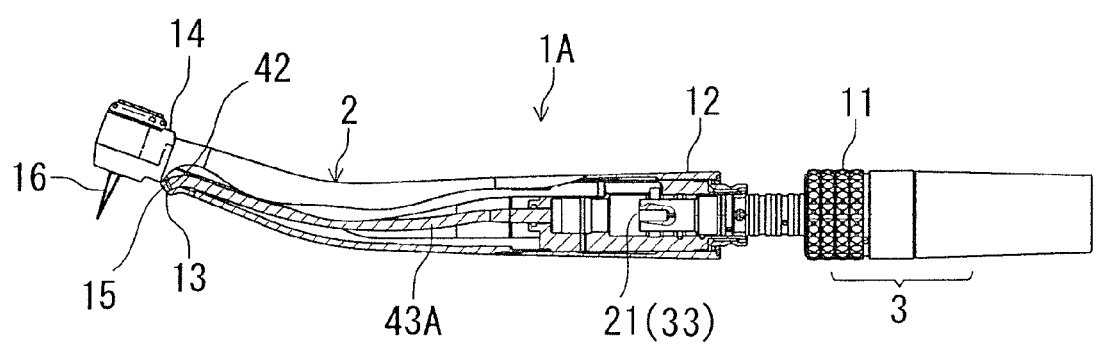
FIG. 18 is a partial cut-away schematic explanatory view illustrating a connection tube portion which can be attached to and detached from the handpiece body in the modification example of the handpiece with a built-in camera according to Embodiment 1 of the invention.

A handpiece 1A with a built-in camera of Embodiment 2 is configured of an air turbine-driven type as illustrated in FIGS. 12, 13, and 18, and like elements similar to those of the case of Embodiment 1 are denoted by like reference numerals.

The basic structure of the handpiece 1A with a built-in camera of Embodiment 2 is the same as that of the case of Embodiment 1 but is characterized in that the color camera module 21 is disposed at the center portion of the connection tube portion 11 which is rotatably and detachably joined to the handpiece body tube portion 12 of the handpiece body 2, the objective lens 42 is disposed to face the light receiving port provided in the head portion with a predetermined interval therebetween, and a rod fiber 43A is disposed in a state in which the exit end thereof faces the condensing lens unit 33 included in the color camera module 21 with a predetermined interval therebetween.

In addition, in the handpiece 1A with a built-in camera, as illustrated in FIGS. 12 and 18, the condensing lens unit 33 included in the color camera module 21 is mounted to the connection tube portion 11 which is detachably joined to the handpiece body tube portion 12 included in the grip portion 3 such that the color camera module 21 can be stored and mounted inside the handpiece body 2 by joining the connection tube portion 11 to the handpiece body tube portion 12 and the color camera module 21 can be detached from the inside of the handpiece body 2 by removing the connection tube portion 11 from the handpiece body tube portion 12.

In addition, as the configuration of rotatably and detachably joining the connection tube portion 11 to the inside of the handpiece body 2, a well-known configuration in which a handheld member 2 or a joint portion HJ in FIG. 1 of Patent Documents 5 and 6 suggested by the applicant is screwed to an handpiece HP is employed. Therefore, the color camera module 21 (the condensing lens unit 33) can be stored in or detached from the handpiece body 2 by an operation of attaching or detaching the color camera module 21 (the condensing lens unit 33) attached to the connection tube portion 11 to or from the handpiece body tube portion 12 of the connection tube portion 11.

In addition, description of the driving system of the cutting tool 16 will be omitted.

As illustrated in FIG. 13, as the rod fiber 43A, like the case of the rod fiber 43, a rod fiber having a step-index type structure in which multi-component glass is used for all of the core, the cladding, and the skin tube to provide different refractive indexes in stages, and having optical characteristics of a light receiving angle of about 70 degrees and a numerical aperture (NA) of 0.57 is employed.

In addition, in the rod fiber 43A, the shape of the light exit end thereof has, for example, a fiber diameter of Φ2=about 2.4 mm, and the shape of the light incidence end is, for example, an oval shape having a major axis of about 2.85 mm and a minor axis of about 2.00 mm.

The other configurations of the handpiece 1A with a built-in camera of Embodiment 2 are similar to those of the case of Embodiment 1.

According to the handpiece 1A with a built-in camera of Embodiment 2, as in the case of Embodiment 1, photographing light which is incident onto the objective lens 42 from the affected area P can be reliably guided to the color image sensor 38 and conversion of the light into a color image can be realized. Therefore, it is possible to provide the handpiece 1A with a built-in camera having a high practical value.

In addition, according to Embodiment 2, as in the case of Embodiment 1, the focus range of the condensing lens unit 33 is set to 3 to 50 mm. Therefore, when a treatment is performed by using the handpiece 1 with a built-in camera, a range in which a clear color image of the affected area P can be obtained is wide. Even from this point, the handpiece 1A with a built-in camera having a high practical value can be provided.

Next, a handpiece 1B with a built-in camera according to a modification example of the air turbine-driven type handpiece 1A with a built-in camera of Embodiment 2 will be described with reference to FIG. 14.

The basic configuration of the handpiece 1B with a built-in camera according to the modification example is the same as that of the case of the handpiece 1A with a built-in camera of Embodiment 2 but is characterized in that an anti-fogging mechanism is added to the region of the light receiving port 13, that is, the outer surface of the transparent glass plate 15.

That is, a water flow passage 81 and an air flow passage 80 are provided on the handpiece body 2 side, a ring 91 is fixed to the lower surface of the head portion 14 via a nut 32 at a position near the position where the cutting tool 16 is attached, a water ejection hole 93 is formed on the outside of the lower surface of the ring 91, and an air ejection hole 94 is provided on the inside adjacent to the water ejection hole 93.

In addition, the water ejection hole 93 is connected to the water flow passage 81 via a peripheral groove 95 formed on the head portion 14 side, and the air ejection hole 94 is connected to the air flow passage 80 via a peripheral groove 96.

Furthermore, the air flow passage 80 branches to provide an anti-fogging air flow passage 82 included in the anti-fogging mechanism directed toward the transparent glass plate 15. By the air blown from the anti-fogging air flow passage 82 toward the transparent glass plate 15, fog on the transparent glass plate 15 that is formed when cutting work is performed on the affected area P by the handpiece 1B with a built-in camera is removed such that photographing light from the affected area P is incident onto the objective lens 42 in a clear state and is guided to the color image sensor 38 to image a clear color image.

Description of the system for supplying water and air to the water flow passage 81 and the air flow passage 80 and the internal structure of the head portion 14 will be omitted.

Figure 14:
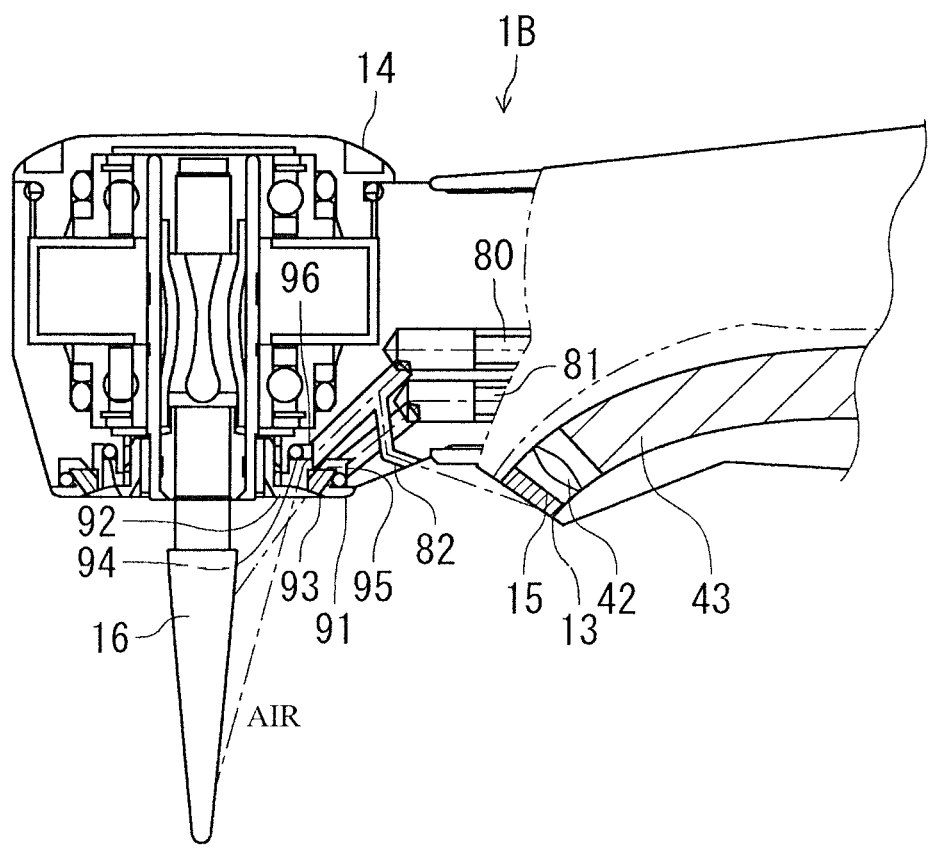
FIG. 14 is a partial cut-away schematic enlarged view illustrating a modification example of a handpiece body including a head portion in the handpiece with a built-in camera according to Embodiment 2 of the invention.

In addition, even in the case of the handpiece 1 with a built-in camera of Embodiment 1, it is natural that a configuration in which the anti-fogging mechanism illustrated in FIG. 14 is added can be employed.

Next, a modification example of the handpiece 1 with a built-in camera of Embodiment 1 will be described with reference to FIGS. 15 and 16.

Figure 15:
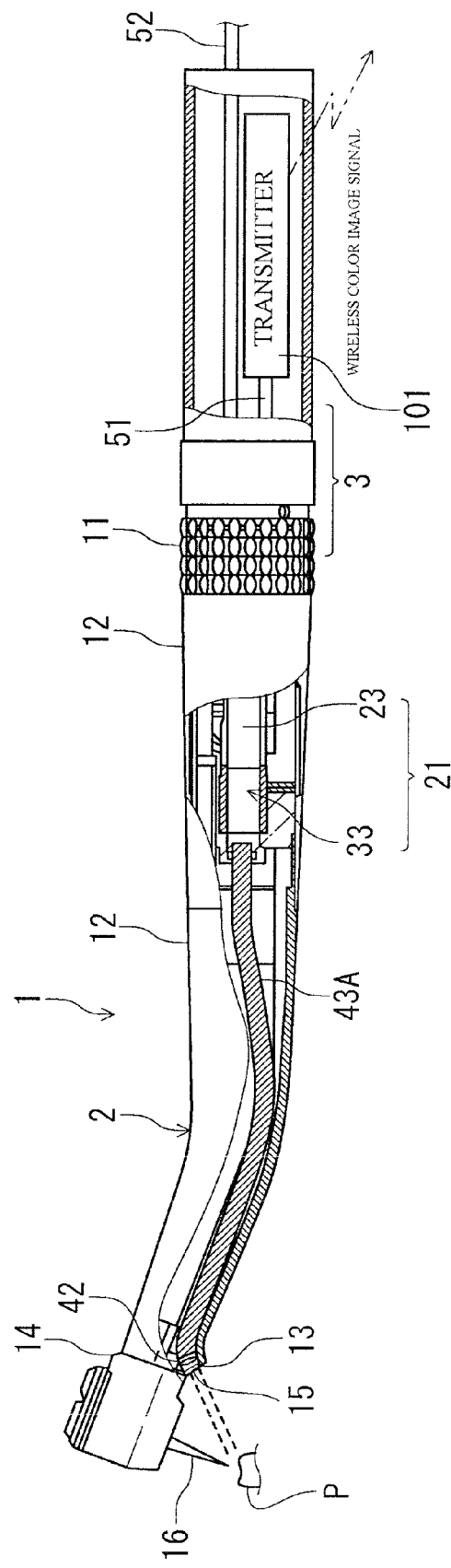
FIG. 15 is a partial cut-away front view illustrating a modification example of the handpiece with a built-in camera according to Embodiment 1 of the invention.

In the modification example, a configuration in which a transmission side transmitter 101 based on, for example, the Bluetooth standard (one of the wireless communication protocols) that is connected to the signal output cable 36 as illustrated in FIG. 15 is provided in the grip portion 3 in the handpiece 1 with a built-in camera and a reception side transmitter 102 based on, for example, the Bluetooth standard is added to the drive control unit 61 is employed, and the color image signal of the affected area P imaged by the camera unit 31 is wirelessly transmitted from the transmitter 101 to the transmitter 102.

As the drive control unit 61, a control unit to which the handpiece 1 with a built-in camera is connected, a computer based on the Bluetooth standard, and the like may be exemplified.

Figure 16:
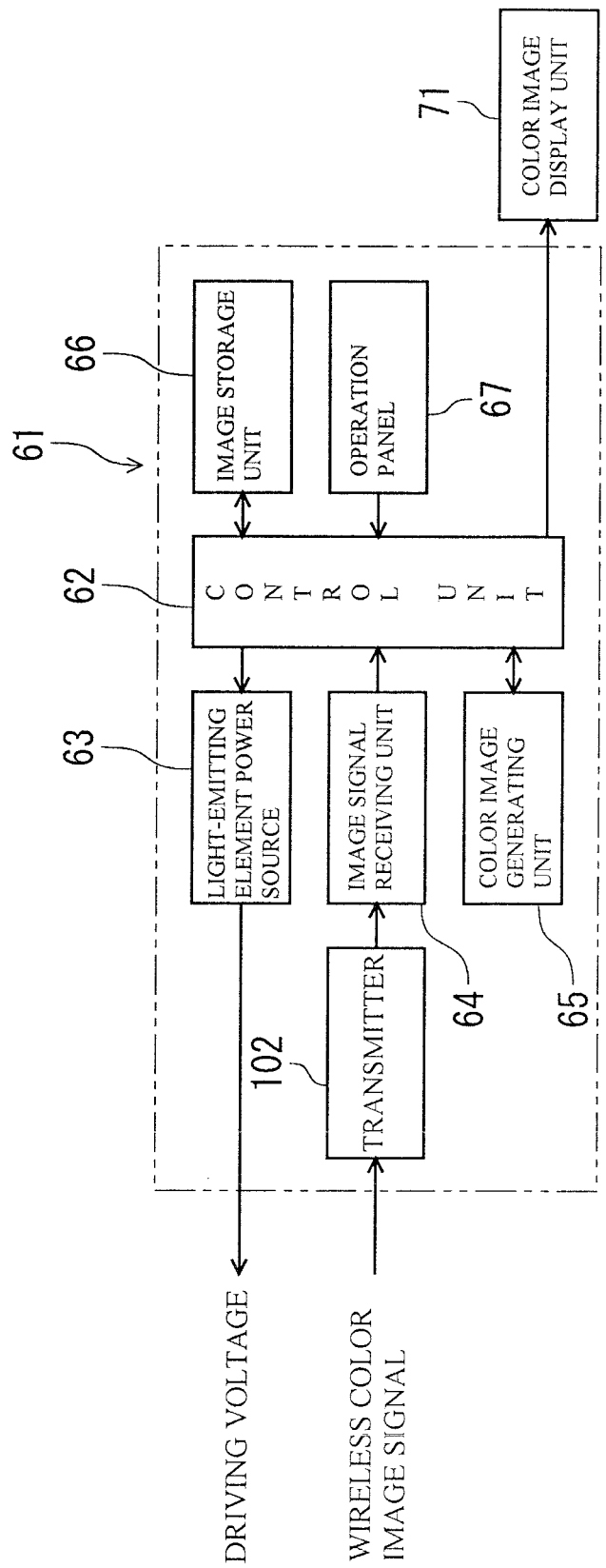
FIG. 16 is a block diagram illustrating a modification example of the drive control unit connected to the handpiece with a built-in camera according to Embodiment 1 of the invention.

According to the modification example illustrated in FIGS. 15 and 16, the same specification as the driving voltage of the light-emitting element 24 (for example, a driving voltage of DC 3.3 V) is employed as the driving voltage of the transmission side transmitter 101, and thus power wiring of the transmission side transmitter 101 can be performed by using two electric wires of the light-emitting element driving cable 52. Accordingly, there is no need to perform cabling dedicated to the transmission side transmitter 101, resulting in a reduction in the number of wires and a reduction in the number of occurrences of an inconvenient circumstance such as cable disconnection.

Furthermore, even in the case of the handpiece 1B with a built-in camera of Embodiment 2, it is natural that the same wireless transmission means as that of the case of the modification example illustrated in FIG. 15 can be employed.

Next, a handpiece 1C with a built-in camera according to another modification example of the air turbine-driven type handpiece 1A with a built-in camera of Embodiment 2 will be described with reference to FIG. 17.

The basic configuration of the handpiece 1C with a built-in camera according to the modification example is the same as that of the case of the handpiece 1A with a built-in camera of Embodiment 2 but is characterized in that, similarly to the case illustrated in FIG. 14, an anti-fogging mechanism for the outer surface of the transparent glass plate 15 is added to the periphery of the light receiving port 13.

That is, a configuration in which the air flow passage 80 having the same structure as that of the case illustrated in FIG. 14 branches to provide an anti-fogging air flow passage 82a having a structure that occupies positions that surround parts of the outside of the light receiving port 13 (the outside of the transparent glass plate 15) so as to eject air from an opening 82b of the anti-fogging air flow passage 82a toward the front side of the transparent glass plate 15 is employed.

Figure 17:
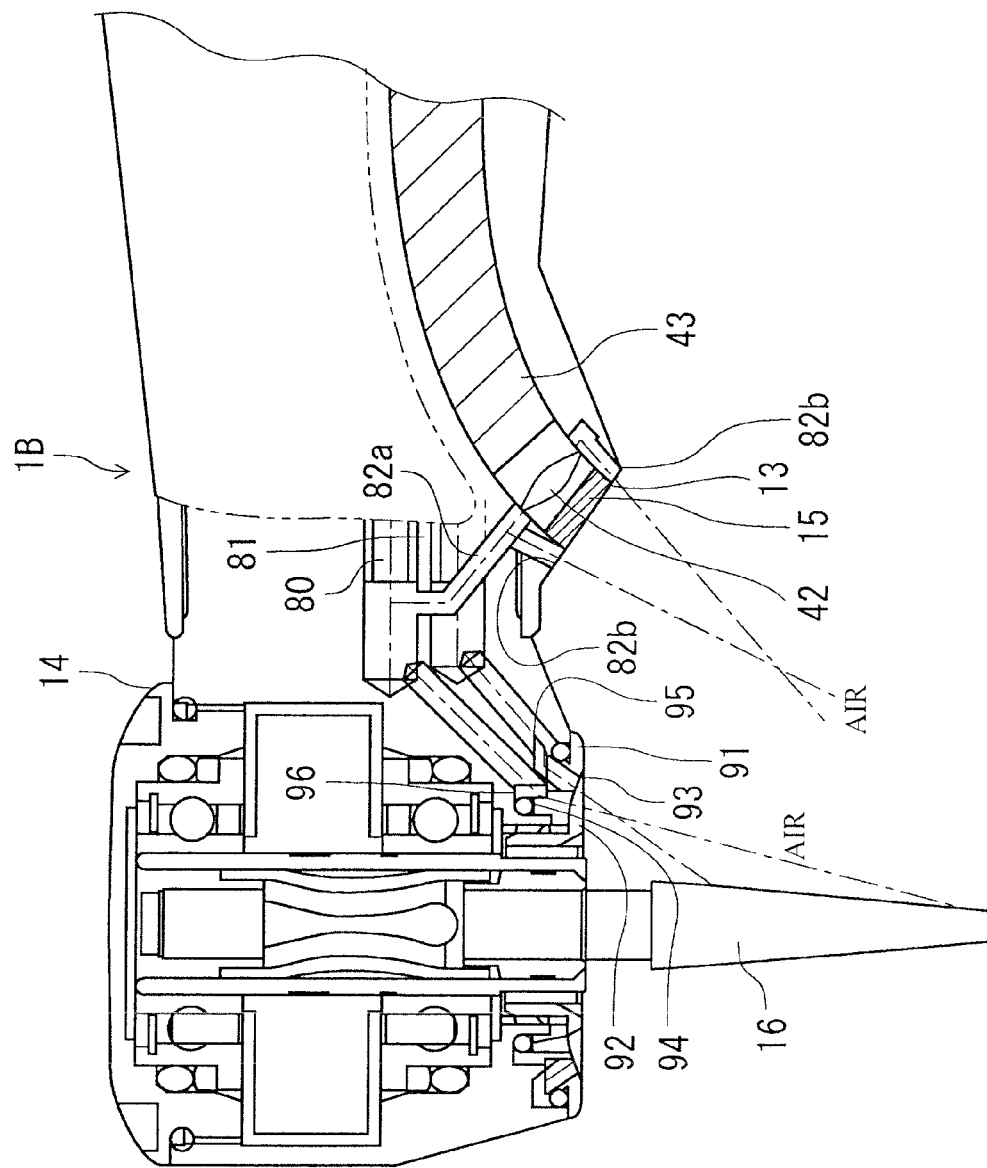
FIG. 17 is a partial cut-away schematic enlarged view illustrating another modification example of the handpiece body including the head portion in the handpiece with a built-in camera according to Embodiment 2 of the invention.

According to the anti-fogging mechanism illustrated in FIG. 17, by an air curtain effect of the air ejected from the opening 82b of the anti-fogging air flow passage 82a, fogging of the transparent glass plate 15 caused by spray or water drops generated during the cutting work by the handpiece 1C with a built-in camera is prevented. Therefore, photographing light from the affected area P is incident onto the objective lens 42 in a clear state while securing visibility and is guided to the color image sensor 38 and thus a clear color image can be imaged.

Furthermore, an anti-fogging mechanism provided with both of the anti-fogging mechanism illustrated in FIG. 14 which blows air from the anti-fogging air flow passage 82 toward the transparent glass plate 15 and the anti-fogging mechanism illustrated in FIG. 17 and configured to provide the anti-fogging air flow passage 82a and eject air from the opening 82b of the anti-fogging air flow passage 82a toward the front side of the transparent glass plate 15 may also be employed.

In this configuration, photographing light from the affected area P is incident onto the objective lens 42 in a clear state while securing better visibility and is guided to the color image sensor 38 and thus a clear color image can be imaged.

The invention is also applicable to, in addition to the above-described cases, a spray type handpiece, an ultrasonic scaler, and the like.

The invention claimed is:

1. A handpiece with a built-in camera comprising:
   a micromotor-driven handpiece body which includes a cutting tool attached to a head portion thereof, and a light receiving port provided at a position within a first threshold distance from the cutting tool;
   a grip portion which is detachably connected to the handpiece body; and
   a color camera module which is stored inside the handpiece body,
   wherein the color camera module comprises a camera unit having a condensing lens unit and a color image sensor that outputs a color image signal, and an arbitrary number of LEDs which are circularly arranged around a periphery of the camera unit, and the color camera module is attached to an inner wall portion of the handpiece body within a second threshold distance from the grip portion;
   and the handpiece with the built-in camera further comprising:
   an objective lens which faces the light receiving port provided in the head portion, and a rod fiber which is attached to the inner wall portion of the handpiece body with an incidence end of the rod fiber facing the objective lens with a predetermined interval therebetween and an exit end of the rod fiber facing the condensing lens unit with a predetermined interval therebetween, and
   a photographing optical system which transmits imaging light of an affected area to the camera unit via the objective lens and the rod fiber.

2. The handpiece with a built-in camera according to claim 1,
   wherein the interval between the objective lens and the incidence end of the rod fiber is configured to allow photographing light from the objective lens to be substantially received by a light receiving angle of the rod fiber, and the interval between the exit end of the rod fiber and the condensing lens unit is configured to allow light that exits from the rod fiber to be substantially received by the viewing angle of the condensing lens unit.

3. The handpiece with a built-in camera according to claim 1, further comprising:
   an anti-fogging mechanism which blows air toward a region of the light receiving port for anti-fogging of the light receiving port.

4. The handpiece with a built-in camera according to claim 1, further comprising:
   an anti-fogging mechanism which blows air toward a front side of the light receiving port and secures visibility to imaging light that is incident onto the light receiving port due to an air curtain effect.

5. The handpiece with a built-in camera according to claim 1,
   wherein the condensing lens unit has a focus range set to 3 to 50 mm.

6. The handpiece with a built-in camera according to claim 1, further comprising:
   an anti-fogging mechanism which blows air toward a region of the light receiving port for anti-fogging of the light receiving port.

7. The handpiece with a built-in camera according to claim 1, further comprising:
   a wireless communication system for allowing an image signal imaged by the camera unit to be wirelessly communicated with the outside.

8. A treatment method by a handpiece with a built-in camera, comprising:
   performing a treatment while viewing a clear color image of a treatment site by using the handpiece with a built-in camera according to claim 1.

9. A handpiece with a built-in camera comprising:
   an air turbine-driven handpiece body which includes a cutting tool attached to a head portion thereof, and a light receiving port provided at a position within a first threshold distance from the cutting tool;
   a grip portion which is detachably connected to the handpiece body; and
   a color camera module which is stored inside the handpiece body,
   wherein the color camera module includes a camera unit having a condensing lens unit and a color image sensor that outputs a color image signal, and an arbitrary number of LEDs which are circularly arranged around a periphery of the camera unit, and the color camera module is disposed at a center portion of the handpiece body;
   and the handpiece with the built-in camera further comprising:
   an objective lens which faces the light receiving port provided in the head portion, and a rod fiber which is disposed in the handpiece body with an incidence end of the rod fiber facing the objective lens with a predetermined interval therebetween and an exit end of the rod fiber facing the condensing lens unit with a predetermined interval therebetween, and
   a photographing optical system which transmits imaging light of an affected area to the camera unit via the objective lens and the rod fiber.

10. The handpiece with a built-in camera according to claim 9,
    wherein the condensing lens unit has a focus range set to 3 to 50 mm.

11. The handpiece with a built-in camera according to claim 9,
    wherein the interval between the objective lens and the incidence end of the rod fiber is configured to allow photographing light from the objective lens to be substantially received by a light receiving angle of the rod fiber, and the interval between the exit end of the rod fiber and the condensing lens unit is configured to allow light that exits from the rod fiber to be substantially received by the viewing angle of the condensing lens unit.

12. The handpiece with a built-in camera according to claim 9, further comprising:
an anti-fogging mechanism which blows air toward a region of the light receiving port for anti-fogging of the light receiving port.

13. The handpiece with a built-in camera according to claim 9, further comprising:
an anti-fogging mechanism which blows air toward a front side of the light receiving port and secures visibility to imaging light that is incident onto the light receiving port due to an air curtain effect.

14. The handpiece with a built-in camera according to claim 9, further comprising:
a wireless communication system for allowing an image signal imaged by the camera unit to be wirelessly communicated with the outside.

15. A treatment method by a handpiece with a built-in camera, comprising:
performing a treatment while viewing a clear color image of a treatment site by using the handpiece with a built-in camera according to claim 9.

* * * * *